Figure 1:
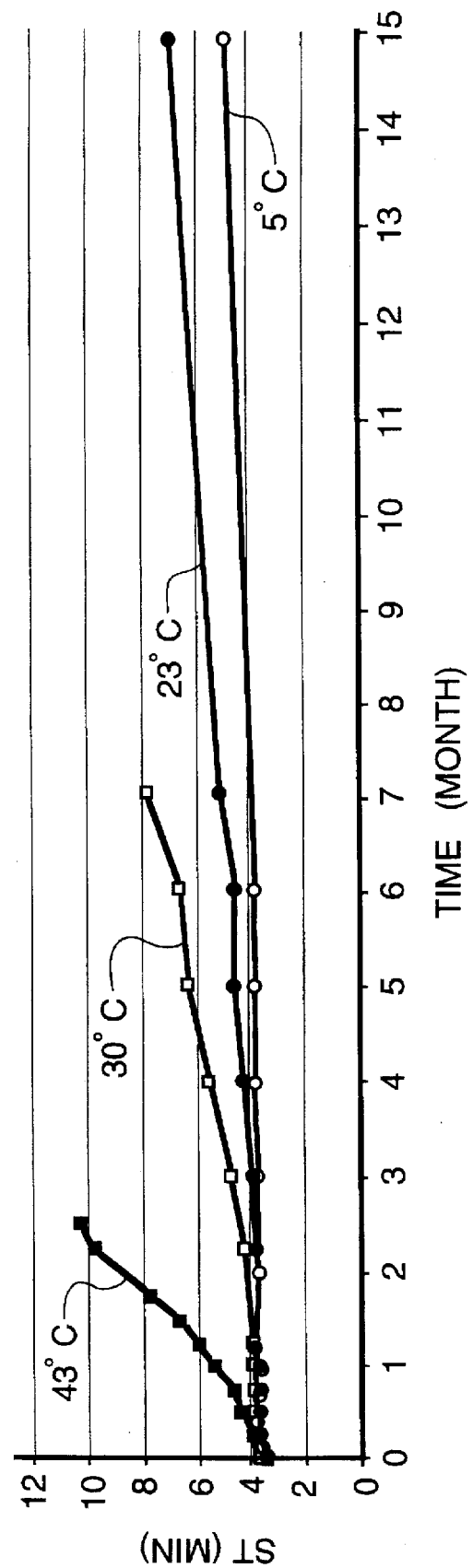

United States Patent [19]

Klee et al.

[11] Patent Number: 5,688,883
[45] Date of Patent: Nov. 18, 1997

[54] POLYMERIZABLE COMPOSITION

[75] Inventors: Joachim E. Klee, Radolfzell; Uwe Walz, Constance, both of Germany

[73] Assignee: Dentsply GmbH, Dreieich, Germany

[21] Appl. No.: 404,402

[22] Filed: Mar. 14, 1995

[51] Int. Cl.$^6$ .............................. C08F 4/44; C08F 4/34; C08F 20/10; C09J 133/06
[52] U.S. Cl. ................ 526/141; 526/227; 526/230.5; 526/328
[58] Field of Search ...................... 526/141, 227, 526/230.5, 328

[56] References Cited

U.S. PATENT DOCUMENTS

| | | | |
|---|---|---|---|
| 3,200,142 | 8/1965 | Bowen | 260/468 |
| 3,293,233 | 12/1966 | Erchak, Jr. et al. | 260/94.9 |
| 3,539,533 | 11/1970 | Lee, II et al. | 260/47 |
| 3,709,866 | 1/1973 | Waller | 260/27 R |
| 3,815,239 | 6/1974 | Lee, Jr. et al. | 32/15 |
| 3,835,090 | 9/1974 | Gander et al. | 260/42.15 |
| 3,853,962 | 12/1974 | Gander | 260/486 R |
| 3,889,385 | 6/1975 | Dougherty | 32/12 |
| 3,926,906 | 12/1975 | Lee, II et al. | 260/42.53 |
| 4,150,012 | 4/1979 | Joos | 260/42.15 |
| 4,182,035 | 1/1980 | Yamauchi et al. | 433/228 |
| 4,383,826 | 5/1983 | Butler et al. | 433/228 |
| 4,427,823 | 1/1984 | Inagaki et al. | 524/833 |
| 4,431,421 | 2/1984 | Kawahara et al. | 433/228 |
| 4,446,246 | 5/1984 | McGinniss | 502/155 |
| 4,467,079 | 8/1984 | Hechenberger et al. | 526/90 |
| 4,547,531 | 10/1985 | Waknine | 523/116 |
| 4,557,848 | 12/1985 | Sung et al. | 252/51.5 R |
| 4,866,146 | 9/1989 | Janda et al. | 526/213 |
| 4,872,936 | 10/1989 | Engelbrecht | 156/307.3 |
| 5,166,117 | 11/1992 | Imai et al. | 502/169 |
| 5,252,629 | 10/1993 | Imai et al. | 523/118 |

FOREIGN PATENT DOCUMENTS

| | | |
|---|---|---|
| 0 115 410 | 8/1984 | European Pat. Off. . |
| 0 115 948 | 8/1984 | European Pat. Off. . |
| 0 120 559 | 10/1984 | European Pat. Off. . |
| 0 277 413 | 8/1988 | European Pat. Off. . |
| 0 335 645 | 10/1989 | European Pat. Off. . |
| 1 089 198 | 3/1955 | France . |
| 1 003 448 | 8/1958 | Germany . |
| 39 28 987 | 3/1991 | Germany . |
| 95/22955 | 8/1995 | WIPO . |

OTHER PUBLICATIONS

Antonucci et al; Journal of Dental Research 58(9): pp. 1887–1899, Sep. 1979; New Initiator Systems for Dental Resins Based on Ascorbic Acid.

Beaunez et al; Journal of Polymer Science: Part A: Polymer Chemistry, vol. 32, pp. 1459–1469 (1994).

Lal et al; Journal of Polymer Science: vol. XXIV, pp. 75–84 (1957) New Polymerization Catalysts for Methyl Methacrylate.

*Primary Examiner*—Joseph L. Schofer
*Assistant Examiner*—Wu C. Cheng
*Attorney, Agent, or Firm*—Dale R. Lovercheck; James B. Bieber

[57] ABSTRACT

The invention provides a polymerizable composition formed by mixing a liquid and a powder composition. The liquid composition includes a peroxide, which decomposes by at most fifty percent by weight of the peroxide within 10 hours at a temperature of at least 75° C., and a polymerizable monomer. The powder composition comprising a proton donor, and a metal containing compound. The polymerizable composition has from 0.2 to 5 percent by weight of the peroxide, from 5 to 99 percent by weight of the polymerizable monomer, and from 0.1 to 3 percent by weight of the proton donor, and from 0.02 to 3 percent by weight of the metal containing compound. The polymerizable composition has an initial setting time and a storage setting time after storage of the first (liquid) composition for at least 12 months at a temperature of at least 23° C. The initial setting time is within 2 minutes of the storage setting time.

31 Claims, 4 Drawing Sheets

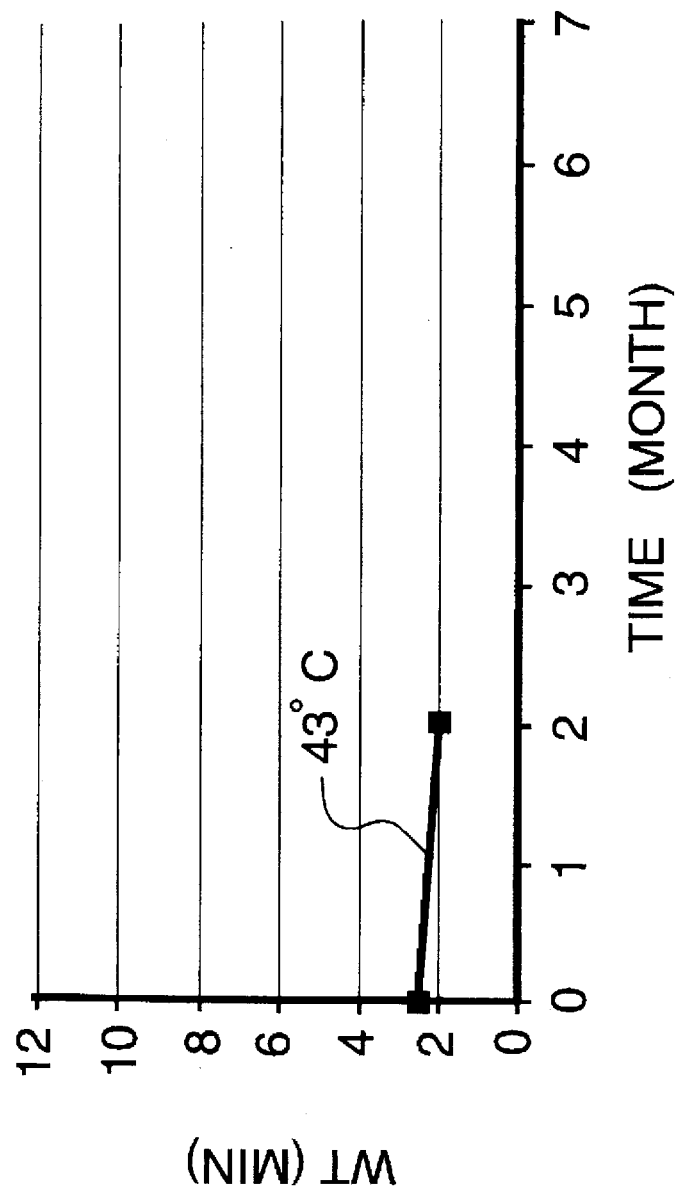

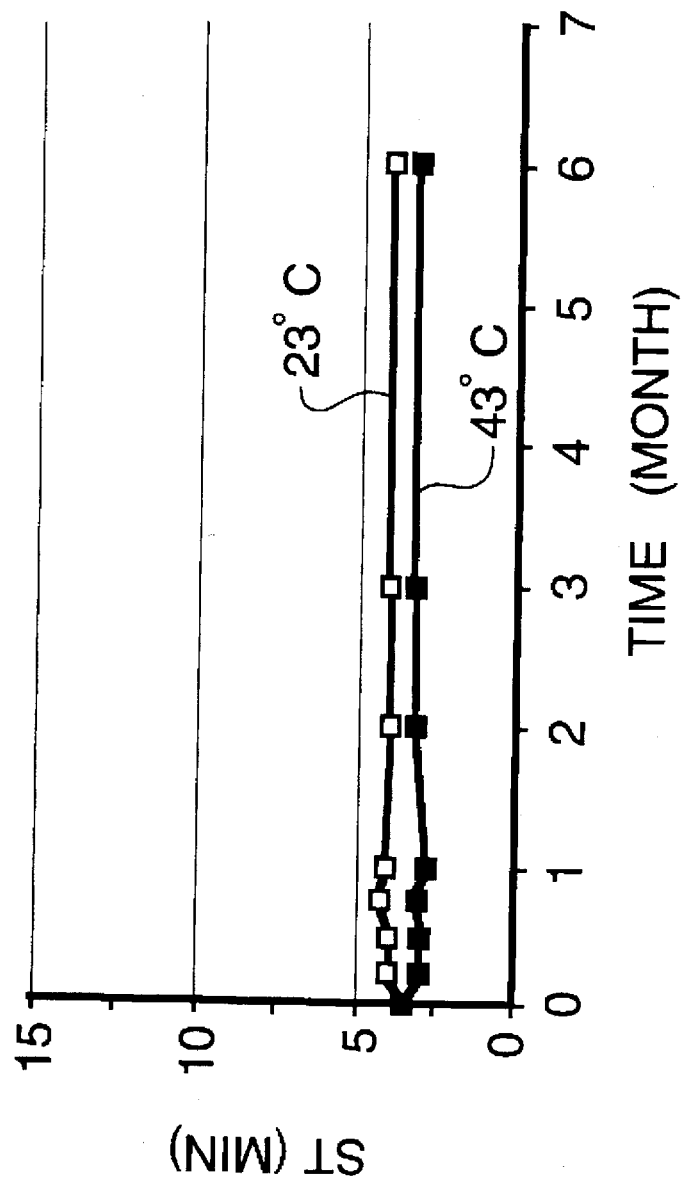

POLYMERIZABLE COMPOSITION

The invention relates to polymerizable compositions and polymerization initiating compositions therefor. The invention provides a polymerizable dental/medical composition having a polymerization initiator composition which is stable at 23° C. for at least eighteen months. The invention provides dental composite, dental cement and dental sealer compositions. A polymerizable composition is provided in accordance with the invention which includes from 0.2 to 5 percent by weight of a peroxide, which decomposes by at most fifty percent by weight of the peroxide within 10 hours at a temperature of at least 75° C., 0.1 to 3 percent by weight of the proton donor, from 0.02 to 3 percent by weight of the metal containing compound and from 5 to 99 percent by weight of a polymerizable monomer. The polymerizable composition has an initial setting time which preferably is within 2 minutes of the setting time after storage for at least 12 months at a temperature of at least 23° C.

It is an object of the invention to provide a polymerizable composition which has from 0.2 to 5 percent by weight of the peroxide, from 5 to 99 percent by weight of the polymerizable monomer, and from 0.1 to 3 percent by weight of the proton donor, from 0.02 to 3 percent by weight of the metal containing compound.

It is an object of the invention to provide a polymerizable composition including from 0.2 to 5 percent by weight of a peroxide, which decomposes by at most fifty percent by weight of the peroxide within 10 hours at a temperature of at least 75° C., and from 5 to 99 percent by weight of a polymerizable monomer.

It is an object of the invention to provide polymerizable composition having an initial setting time which is within 2 minutes of a storage setting time after storage for at least 12 months at a temperature of at least 23° C.

Joos in U.S. Pat. No. 4,150,012 discloses discernible dental sealant. Yamauchi et al in U.S. Pat. No. 4,182,035 discloses adhesive compositions for the hard tissues of the human body. Butler et al in U.S. Pat. No. 4,383,826 discloses adducts of diisocyanates and methacryloyl alkyl ethers, alkoxybenzenes or alkoxycycloalkanes, compositions containing such compounds, and method of use thereof. Kawahara et al in U.S. Pat. No. 4,431,421 discloses dental restorative composition. McGinniss in U.S. Pat. No. 4,446,246 discloses catalyst systems for two-pack acrylic adhesive formulations. Hechenberger et al in U.S. Pat. No. 4,467,079 discloses curing compositions containing redox indicators. Waknine in U.S. Pat. No. 4,547,531 disclose two component (paste-paste) self-curing dental restorative material. Janda et al in U.S. Pat. No. 4,866,146 discloses thermosetting dental materials. Engelbrecht in U.S. Pat. No. 4,872,936 disclose polymerizable cement mixtures. Imai et al in U.S. Pat. No. 5,166,117 discloses polymerization initiator composition controlling polymerization at interface and curable composition containing same. Imai et al in U.S. Pat. No. 5,252,629 discloses adhesives for dentin. J. Lal et al. in J.Polym. Sci. 24 (1957) 75 discloses new polymerization catalysts for methyl methacrylate.

A polymerization initiator is described by J. M. Antonucci et al. in J. Dental Research 58 (9) 1887–1899, September 1979 which includes peroxide, a metal salt and ascorbic acid. The Antonucci initiator discolors to yellow. Barbituric acid or thiobarbituric acid are used in U.S. Pat. No. 5,166,117. Polymerization initiators comprising BPO, a sulfinate and an amine are disclosed by Kurraray in EP 0115410, EP 0115948, EP 0120559, and EP 0277413. Bredereck in DE 1 003 448 discloses polymerization initiators inorganic salts of sulfinic acid, hydrohalogenides and some times peroxide. A polymerization initiator consisting of cumen hydroperoxide, saccharin, copper or iron saccharinate and N,N-di(hydroxyethyl)-p-toluidine is described by G. Sauvet et al. in J. Appl. Polym. Sci., Part A, Polym. Chem. 32 (1994) 1459, 1470.

Prior art compositions which include di-benzoyl peroxide and amine have the disadvantage of thermal-self decomposition of di-benzoyl peroxide (BPO) and/or the discoloration by aromatic amines. Consequently, the problem of thermal decomposition remains unsolved in the prior art.

Setting time as used herein is initiated by mixing a polymerizable composition containing a monomer and a peroxide with a proton donor containing composition containing a proton donor to form a polymerizing composition. Setting time ends upon substantial hardening of the polymerizing composition.

Initial setting time as used herein is the setting time of polymerizing composition formed from the peroxide containing polymerizable composition and the proton donor containing composition which have been made within 1 hour of their being mixed to form the polymerizing composition.

Storage setting time as used herein refers to the setting time of a polymerizing composition formed by mixing the polymerizable composition and the proton donor containing composition. The polymerizable composition is stored for the period stated at the temperature stated, and then are mixed at 23° C. to form a polymerizing composition.

The disadvantages of prior art initiator systems are overcome by use of dental compositions in accordance with the invention.

BRIEF SUMMARY OF INVENTION

The invention provides a polymerizable composition formed by mixing a liquid and a powder composition. The liquid composition includes a peroxide, which decomposes by at most fifty percent by weight of the peroxide within 10 hours at a temperature of at least 75° C., and a polymerizable monomer. The powder composition comprising a proton donor, and a metal containing compound. The polymerizable composition has from 0.2 to 5 percent by weight of the peroxide, from 5 to 99 percent by weight of the polymerizable monomer, and from 0.1 to 3 percent by weight of the proton donor, and from 0.02 to 3 percent by weight of the metal containing compound. The polymerizable composition has an initial setting time and a storage setting time after storage of the first (liquid) composition for at least 12 months at a temperature of at least 23° C. The initial setting time is within 2 minutes of the storage setting time.

DESCRIPTION OF THE INVENTION

The invention provides a polymerizable composition for application to dental teeth, comprising from 0.2 to 5 percent by weight of a peroxide which decomposes by at most fifty percent by weight within 10 hours at a temperature of at least 75° C., 0.1 to 3 percent by weight of the proton donor, and from 0.02 to 3 percent by weight of the metal containing compound and from 10 to 99 percent by weight of a polymerizable monomer. The polymerizable composition preferably includes from 0.02 to 1 percent by weight of an amine. The polymerizable composition preferably has an initial setting time which is within two minutes of the setting time after storage for 12 months at 43° C.

Preferably the polymerizable composition is mixed with a powder comprising a metal containing compound, a proton donor and a filler. In a preferred embodiment the polymerizable composition includes from 10 to 50 percent by weight of the monomer, 50 to 65 percent by weight of a filler and from 0.2 to 5 percent by weight of the peroxide.

Peroxides useful in compositions in accordance with the invention half decompose during 10 hours at temperatures above 75° C. Exemplary of peroxides useful in compositions in accordance with the invention are 2,5-dimethyl-2,5-di (benzoylperoxy)hexane which half decomposes within 10 hours at 100° C.; tert.-butylperoxy-(3,5,5-trimethylhexanoate) which half decomposes within 10 hours at 100° C.; tert.-butylperoxybenzoate which half decomposes within 10 hours at 104° C.; tert.-butylamyl peroxide which half decomposes within 10 hours at 104° C.; di-(tert.-butyl) peroxide half decomposes within 10 hours at 125° C.; and tert.-butylhydro peroxide half decomposes within 10 hours at 170° C.

Preferably the peroxide is a diacyl peroxide, a perester, a perketale, a peroxy dicarbonate, a dialkyl peroxide, a ketone peroxide or a alkyl hydroxyperoxide. More preferably the peroxide is selected from the group consisting of 2,5-dimethyl-2,5-di(benzolyperoxy)hexane, tert.-butylamyl peroxide, di-(tert.-butyl) peroxide, cumenhydo peroxide, tert.-butylhydro peroxide, tert.-butylperoxy-(3,5,5-trimethylhexanoate), tert-butyl peroxy benzoate and tert.-butylperoxy-2-ethylhexyl carbonate.

Preferably the proton donors is an acid, a phenol, a hydroxy alkene or an acid amine. More preferably the proton donors is a Brönsted acid, sulfinic acid, oxalic acid, picric acid, ascorbic acid, barbituric acid or thiobarbituric acid.

Amines preferred for use in compositions in accordance with the invention include alkyl aryl amines, dialkyl aryl amines, trialkyl amines or derivatives therefrom. Preferred are N,N-dihydroxyethyl -p-toluidine, N,N-diethyl-p-benzoic acid ethyl ester, and tributylamine.

Preferably the metal of the metal containing compound is copper, silver, cerium, iron, chromium, cobolt, nickel, vanadium or manganese. Metal containing compounds preferred for use in compositions in accordance with the invention include salts of a metal or an organo-metalic compound. Preferred are salts of a metal or an organo-metalic compound derived from copper, silver, cerium, iron, chromium, cobolt, nickel, vanadium or manganese. More preferably the metal containing compound is an acetate, salicylate, naphenoate, thiourea complex, acetylacetonate or ethylene tetramine acetic acid. Most preferred are copper thiourea complex, copper acetyl acetonate, copper saccarinate, copper naphenoate, nickel acetyl acetonate, nickel salicylate, vanadium saccarinate, chromium salicylate, chromium acetate.

Monomers having at least one polymerizable group are preferred for use in compositions in accordance with the invention. These include mono- or polyfunctional (meth) acrylates and macromonomers. Exemplary of such monomers are the macromonomers disclosed in U.S. Patent application serial number 08/359,217 filed Dec. 19, 1994 (case 1731) the disclosure of which is incorporated herein by reference. Preferred monomers include 2,2-Bis-[p-(2-hydroxy-3-methacryloyloxypropoxy)-phenyl]-propane, 7, 7, 9-trimethyl-4, 13-dioxo-3, 14-dioxa-5, 12-diazahexadecan-1, 16-diol methacrylate, dipentaer-thrytrolpentamethacrylate monophosphate, α,ω-methacryloyl terminated epoxide-amine macromonomers, α,ω-methacryloyl terminated epoxide-carboxylic acid macromonomers, α,ω-methacryloyl terminated epoxide-phenol macromonomers.

Preferably the polymerizable monomer is a macromonomer, a mono- or polyfunctional (meth) acrylate, such as a polyalkylenoxide di- or poly(meth)acrylate, an urethane di- or poly (meth) acrylate, a vinyl-, vinylen- or vinyliden-, acrylate- or methacrylate substituted spiroorthoester, a spiroorthocarbonate or a bicyloorthoester. Preferably the monomer is diethylenglycol dimethacrylate, triethylenglycol dimethacrylate, 3,(4),8,(9)-dimethacryloyloxymethyltricyclodecane, dioxolan bismethacrylate, glycerol trimethacrylate, or furfuryl methacrylate. Preferably the monomer comprises an amount of 5 to 80 percent by weight of the composition.

Preferably the polymerizable composition includes a filler and a stabilizer. Preferably the filler is an inorganic filler and/or an organic filler. Preferred fillers for use in compositions in accordance with the invention include inorganic fillers such as $La_2O_3$, $ZrO_2$, $BiPO_4$, $CaWO_4$, $BaWO_4$, $SrF_2$, $Bi_2O_3$, glasses or an organic fillers, such as polymer granulate or a combination of organic/or inorganic fillers.

A cement in accordance with a preferred embodiment of the invention for dental and/or medical use includes from about 10 to 30 percent by weight of a monomer having at least one polymerizable group, from about 15 to 35 percent by weight of a polymerizable monomer as diluent and a stabilizer, from about 50 to 65 percent by weight of a filler and from about 0.34 to 12 percent by weight of the polymerization initiator component(s).

A composite composition in accordance with a preferred embodiment of the invention for dental and/or medical use includes from about 5 to 25 percent by weight of a monomer having at least one polymerizable group, from about 5 to 20 percent by weight of a polymerizable monomer as diluent and a stabilizer, from about 50 to 85 percent by weight of a filler and from about 0,34 to 12 percent by weight of the polymerization initiator component(s).

A dental/medical sealer in accordance with a preferred embodiment of the invention for dental and/or medical use includes from about 15 to 55 percent by weight of a monomer having at least one polymerizable group, from about 20 to 40 percent by weight of a polymerizable monomer as diluent and a stabilizer and from about 10 to 50 percent by weight of a filler and 0.34 to 12 percent by weight of the polymerization initiator component(s).

The preferred distribution for manufacture and storage of compositions in accordance with the invention is between a separately contained liquid composition and a powder composition. The liquid preferably includes a monomer having at least one polymerizable group, polymerizable monomer as diluent, peroxide, and a stabilizer. The powder composition preferably includes a filler, a proton donor, metal containing compound, and an amine.

Alternatively the liquid composition includes a monomer having at least one polymerizable group, polymerizable monomer as diluent, peroxide, amine, and a stabilizer, and the powder includes a filler, a proton donor, and metal containing compound. Surprisingly, the peroxide and the tertiary amine do not react during storing at either 23° C. or 43° C. over a 6 month period of time.

Figure 2:
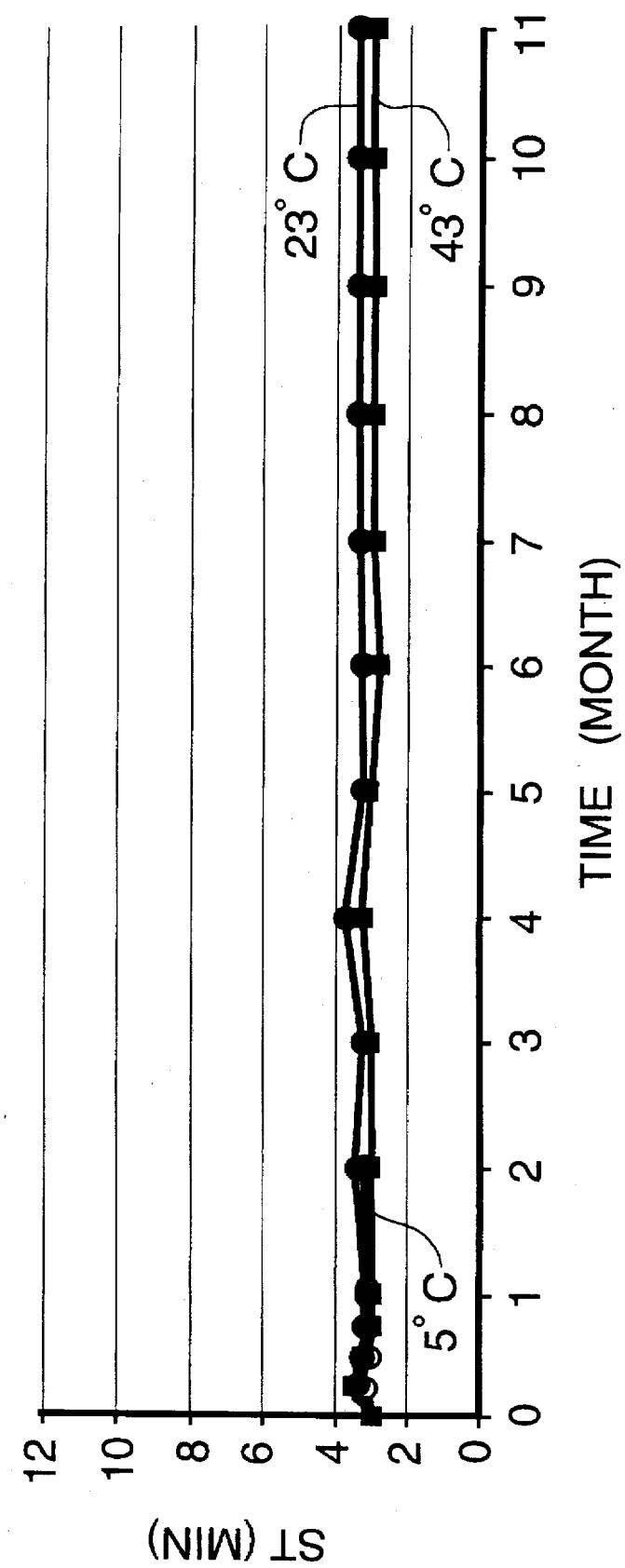

FIG. 1 shows the setting times of the composite of First Comparative Example and stored at 5° C., 23° C., 30° C. and 43° C. FIG. 2 shows the setting times of the composite formed as described in Example 1 and stored at 5° C., 23° C. and 43° C. FIG. 3 shows the setting times of the composite formed as described in Example 2 stored at 43° C. FIG. 4 shows the setting times of the composite formed as described in Example 3 stored at 23° C. and 43° C.

FIRST COMPARATIVE EXAMPLE

Dental Composite Material

A comparative dental composite is formed from a powder and a liquid. The powder is made by homogeneously mixing 68.95 g silylated strontium-alumo-silicate glass and 1.05 g dibenzoyl peroxide. The liquid is made by homogeneously mixing 29.820 g of a percent reacted salt. A salt, and 19.88 g triethylenglycol dimethacrylate, 0.250 g N,N-bis($\beta$-hydroxyethyl)-p-toluidine and 0.05 g 2,6-di-tert.-butyl-p-cresol. The salt (AP-1) is formed by mixing dipentaerthrytrolpentamethacrylate monophosphate (PENTA) and 2-(dimethyl)aminoethyl methacrylate at 0° C. for 5 minutes. To form a polymerizing composite composition powder and liquid are homogeneously mixed in a weight ratio of 1.40 to 1.00. Portions of the powder and liquid are separately stored at 5° C., 23° C., 30° C. and 43° C. for from 0 to 15 months prior to being mixed to form a polymerizing composite composition. The setting times of the portions of polymerizing composite compositions are determined according ISO 9917 and are shown in Table 1 and FIG. 1.

TABLE 1

| storing time | setting time after storing at | | | |
|---|---|---|---|---|
| month | 5° C. | 23° C. | 30° C. | 43° C. |
| 0 | 3.75 | 3.50 | 3.50 | 3.50 |
| 1 | 3.75 | 3.75 | 4.00 | 5.50 |
| 2 | 3.75 | 3.75 | 4.25 | 6.75 |
| 3 | 3.75 | 4.00 | 4.75 | 10.25 |
| 4 | 3.75 | 4.25 | 5.50 | — |
| 5 | 3.75 | 4.50 | 6.25 | — |
| 6 | 3.75 | 4.50 | 6.50 | — |
| 7 | 3.75 | 5.00 | 8.00 | — |
| 8 | 3.75 | 5.00 | | |
| 9 | 3.75 | 5.25 | | |
| 11 | 3.75 | — | | |
| 12 | 3.75 | 5.75 | | |
| 15 | 3.75 | 6.75 | | |

The invention will now be described with reference to examples.

EXAMPLE 1

A dental cement composition is formed from a powder and liquid. The powder is made by homogeneously mixing 69.818 g silylated strontium-alumo-silicate glass, 0.280 g ascorbic acid and 0.042 g copper thio urea complex. The liquid is made by homogeneously mixing 29.670 g of a salt (AP-1), 19.780 g triethylenglycol dimethacrylate, 0.500 g tert-butyl peroxy benzoate, 0.025 g N,N-dihydroxyethyl-p-toluidine and 0.050 g 2,6-di-tert.-butyl-p-cresol. The salt (AP-1) is formed by mixing 100 g PENTA and 16 g 2-(dimethyl) aminoethyl methacryate at 0° C. for 5 minutes. 80 percent of the phosphoric acid moieties of PENTA are reacted with an amino moiety of 2(dimethyl) aminoethyl methacrylate. Portions of the powder and liquid are homogeneously mixed in a weight ratio of 1.4 to 1.0 to form a polymerizing composite composition. The working time of the polymerizing composite composition is 3.00 minutes and the setting time is 3.00 minutes. Prior to mixing the powder and liquid, separate portions of the powder and liquid are stored at 5° C., 23° C. and 43° C. for from 0 to 15 months. The setting times of the portions of polymerizing composite composition determined according ISO 9917 are shown in Table 2 and FIG. 2.

TABLE 2

| storing time | setting time after storing at | | |
|---|---|---|---|
| month | 5° C. | 23° C. | 43° C. |
| 0.00 | 3.00 | 3.00 | 3.00 |
| 0.25 | 3.25 | 3.50 | 3.50 |
| 0.50 | 3.00 | 3.25 | 3.25 |
| 0.75 | 3.00 | 3.25 | 3.00 |
| 1.00 | 3.00 | 3.25 | 3.00 |
| 2.00 | 3.25 | 3.50 | 3.00 |
| 3.00 | 3.25 | 3.25 | 3.00 |
| 4.00 | 3.75 | 3.75 | 3.25 |
| 5.00 | 3.25 | 3.25 | 3.00 |
| 6.00 | 3.25 | 3.25 | 2.75 |
| 7.00 | 3.50 | 3.25 | 3.00 |
| 8.00 | 3.50 | 3.25 | 3.00 |
| 9.00 | 3.50 | 3.25 | 3.00 |
| 10.00 | 3.75 | 3.25 | 3.00 |
| 12.00 | 3.75 | 3.25 | 3.00 |
| 15.00 | 3.75 | 3.25 | 3.00 |

EXAMPLE 2

Dental Cement

A dental cement composition is formed from a powder and liquid. The powder is made by homogeneously mixing 50.038 g silylated strontium-alumo-silicate glass, 0.100 g lithium sulfinate and 0.038 g copper thio urea complex. The liquid is made by homogeneously mixing 25.000 g of a salt, 10.500 g triethylenglycol dimethacrylate, 0.269 g tert.-butyl peroxy (3,5,5-trimethylhexanoate), 0.036 g N,N-dihydroxyethyl-p-toluidine and 0.035 g 2,6-di-tert.-butyl-p-cresol. The salt is formed by mixing 100 g PENTA and 16 g 2-(dimethyl) aminoethyl methacryate at 0° C. for 5 minutes. 80 percent of the phosphoric acid moieties of PENTA are reacted with an amino moiety of 2(dimethyl) aminoethyl methacrylate. Portions of the powder and liquid are homogeneously mixed in a weight ratio of 1.4 to 1.0 to form a polymerizing composite composition. The compressive strength is 243±25 MPa and the E-modulus 2809±309 MPa. The working time of the composition formed in Example 2 is 2.50 minutes. After 8 weeks storing at 43° C. the working time is 2.00 as shown in FIG. 3.

EXAMPLE 3

A dental cement composition is formed from a powder and liquid. The powder is made by homogeneously mixing 37.212 g silylated strontium-alumo-silicate glass, 0.075 g lithium sulfinate and 0.028 g copper thiourea complex. The liquid is made by homogeneously mixing 15.840 g of a salt, 10.560 g triethylenglycol dimethacrylate, 0.200 g tert.-butyl peroxy (3,5,5-trimethylhexanoate), 0.027 g N,N-dihydroxyethyl -p-toluidine and 0.027 g 2,6-di-tert.-butyl-p-cresol. The salt is formed by mixing 100 g PENTA and 16 g 2-(dimethyl) aminoethyl methacryate at 0° C. for 5 minutes. 80 percent of the phosphoric acid moieties of PENTA are reacted with an amino moiety of 2(dimethyl) aminoethyl methacrylate. Portions of the powder and liquid are homogeneously mixed in a weight ratio of 1.4 to 1.0 to form a polymerizing composite composition. The compressive strength of set material is 289±28 MPa and the elastic modulus is 2722±195 MPa. The setting time is 2.75 minutes. Setting times of the composite formed as described in this Example 3 and stored in portions at 23 and 43° C. are shown in FIG. 4.

EXAMPLE 4

A dental cement composition is formed from a powder and liquid. The powder is made by homogeneously mixing 50.140 g silylated strontium-alumo-silicate glass, 0.101 g lithium sulfinate and 0,038 g copper thiourea complex. The liquid is made by homogeneously mixing 25.000 g of a salt, 10.500 g triethylenglycol dimethacrylate, 0.360 g tert.-butyl peroxy (3,5,5-trimethylhexanoate), 0.025 g N,N-dihydroxyethyl-p-toluidine and 0.035 g 2,6-di-tert.-butyl-p-cresol. The salt is formed by mixing 100 g PENTA and 16 g 2-(dimethyl) aminoethyl methacryate at 0° C. for 5 minutes. 80 percent of the phosphoric acid moieties of PENTA are reacted with an amino moiety of 2(dimethyl) aminoethyl methacrylate. Portions of the powder and liquid are homogeneously mixed in a weight ratio of 1.4 to 1.0 to form a polymerizing composite composition.

The compressive strength of set material is 243±25 MPa and the elastic modulus is 2809±390 MPa.

EXAMPLE 5

A dental cement composition is formed from a powder and liquid. The powder is made by homogeneously mixing 141.572 g silylated strontium-alumo-silicate glass, 1.014 g saccharin and 1.420 g copper thio urea complex. The liquid is made by homogeneously mixing 71.800 g of a salt, 28.402 g triethylenglycol dimethacrylate, 1.000 g tert.-butyl peroxy (3,5,5-trimethylhexanoate), 0.100 g N,N-dihydroxyethyl -p-toluidine and 0.100 g 2,6-di-tert.-butyl-p-cresol. The salt is formed by mixing 100 g PENTA and 16 g 2-(dimethyl) aminoethyl methacryate at 0° C. for 5 minutes. 80 percent of the phosphoric acid moieties of PENTA are reacted with an amino moiety of 2(dimethyl) aminoethyl methacrylate. Portions of the powder and liquid are homogeneously mixed in a weight ratio of 1.4 to 1.0 to form a polymerizing composite composition. The working time is 5.00 minutes and the setting time is 4.00 minutes.

EXAMPLE 6

A dental cement composition is formed from a powder and liquid. The powder is made by homogeneously mixing 14.157 g silylated strontium-alumo-silicate glass, 0.127 g barbituric acid and 0.129 g copper thio urea complex. The liquid is made by homogeneously mixing 7.180 g of a salt, 2.840 g triethylenglycol dimethacrylate, 0.100 g tert.-bu-tyl peroxy (3,5,5-trimethylhexanoate), 0.010 g N,N-dihydroxyethyl-p-toluidine and 0.010 g 2,6-di-tert.-butyl-p-cresol. The salt is formed by mixing 100 g PENTA and 16 g 2-(dimethyl) aminoethyl methacryate at 0° C. for 5 minutes. 80 percent of the phosphoric acid moieties of PENTA are reacted with an amino moiety of 2(dimethyl) aminoethyl methacrylate. Portions of the powder and liquid are homogeneously mixed in a weight ratio of 1.4 to 1.0 to form a polymerizing composite composition. The working time is 3.00 minutes and the setting time is 3.50 minutes.

EXAMPLE 7

A dental cement composition is formed from a powder and liquid. The powder is made by homogeneously mixing 14.131 g silylated strontium-alumo-silicate glass, 0.280 g ascorbic acid and 0.042 g copper thio urea complex. The liquid is made by homogeneously mixing 7.000 g of 2,2-Bis-[p-(2-hydroxy-3-methacryloyloxypropoxy)-phenyl]-propane, 3.000 g triethylenglycol dimethacrylate, 0.101 g tert.-butyl peroxy (3,5,5-trimethyl-hexanoate), 0.010 g N,N-dihydroxyethyl-p-toluidine and 0.010 g 2,6-di-tert.-butyl-p-cresol. The salt is formed by mixing 100 g PENTA and 16 g 2-(dimethyl) aminoethyl methacryate at 0° C. for 5 minutes. 80 percent of the phosphoric acid moieties of PENTA are reacted with an amino moiety of 2(dimethyl) aminoethyl methacrylate. Portions of the powder and liquid are homogeneously mixed in a weight ratio of 1.4 to 1.0 to form a polymerizing composite composition. The working time is 3.50 minutes and the setting time is 3.75 minutes.

EXAMPLE 8

A dental cement composition is formed from a powder and liquid. The powder is made by homogeneously mixing 14.131 g silylated strontium-alumo-silicate glass, 0.280 g ascorbic acid and 0.076 g vanadium monobutylphosphite. The liquid is made by homogeneously mixing 7.000 g of 2,2-bis-[p-(2-hydroxy-3-methacryloyloxypropoxy)-phenyl]-propane, 3.000 g triethylenglycol dimethacrylate, 0.101 g tert.-butyl peroxy (3,5,5-trimethyl-hexanoate), 0.010 g N,N-dihydroxyethyl -p-toluidine and 0.010 g 2,6-di-tert.-butyl-p-cresol.

Immediately before use powder and liquid are homogeneously mixed in the weight ratio of 1.40 to 1.00. The setting time of the polymerized dental cement formed is 5.00 minutes.

EXAMPLE 9

A dental cement composition is formed from a powder and liquid. The powder is made by homogeneously mixing 14.131 g silylated strontium-alumo-silicate glass, 0.280 g ascorbic acid and 0.084 g cobalt-II-acetate. The liquid is made by homogeneously mixing 7.000 g of 2,2-bis-[p-(2-hydroxy-3-methacryloyloxypropoxy)-phenyl]-propane, 3.000 g triethylenglycol dimethacrylate, 0.101 g tert.-butyl peroxy (3,5,5-trimethyl-hexanoate), 0.010 g N,N-dihydroxyethyl -p-toluidine and 0.010 g 2,6-di-tert.-butyl-p-cresol. Immediately before use powder and liquid are homogeneously mixed in the weight ratio 1.40 to 1.00. The working time is 6.00 minutes and the setting time of the polymerized dental cement formed is 5.50 minutes.

Macromonomer Preparation

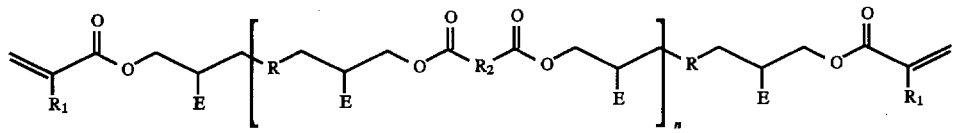

M-1

The macromonomer of formula M-1 wherein n is 1, R is —$OC_6H_4$—$C(CH_3)_2$— $C_6H_4O$—, $R_1$ is —$CH_3$, $R_2$ is —$(CH_2)_4$— and E is —OH is referred to hereinafter as macromonomer M-1 and is prepared by reacting 150.000 g (0.441 mol) bisphenol-A diglycidyl ether, 32.200 g (0.220 mol) adipic acid and 2,000 g triethylbenzylammoniumchloride for four hours at 80° C. while stirring. To the obtained glycidyl terminated prepolymer are added 37.900 g (0.441 mol) methacrylic acid and 0.444 g 2.6-di-tert.-butyl-p-cresol and are reacted for another four hours at 80° C. The methacrylate terminated macromonomer is soluble in organic solvents such as chloroform, DMF and THF. In the IR-spectrum no absorption of epoxide groups at ν=915 and 3050 cm$^{-1}$ is observed. Absorption of ester groups is seen at v=1720 cm$^{-1}$. In the $^1$H NMR spectrum are found signals of the olefinic double bond at $\delta_{(CH_2=)}$=6,137/6,119/6,115 ppm and at $\delta_{(CH_2=)}$=5,582/5,582/5,555/5,548 ppm.

The hydroxyl groups (E) of macromonomer M-1 made by following the procedure of the above paragraph are esterified by adding 16.023 g (160.13 mmol) succinic anhydride to 56.900 g of a macromonomer-triethylenglycol dimethacrylate mixture containing 40.000 g (40.03 mmol) macromonomer M-1 (E is a succinic half ester moiety) and 16.9 g of triethyleneglycol dimethacrylate) while stirring for two hours at 90° C. In the IR-spectrum the esterified macromonomer containing dicarboxylic half ester units shows no absorption of hydroxyl groups at 3400 cm$^{-1}$.

EXAMPLE 10

Dental Adhesive

A dental cement composition is formed from a powder and liquid. The powder is made by homogeneously mixing 50.3639 g silylated strontium-alumo-silicate glass, 2.1546 g silylated strontium alumo-silicate glass comprising 2 percent by weight copper thio urea complex and 1.0773 g silylated strontium-alumo-silicate glass containing 10 percent by weight ascorbic acid. The liquid is made by homogeneously mixing 18.0000 g AP-1 salt prepared as described in Example 1 and comprising 30 percent by weight triethylene glycol dimethacrylate, 4.5000 g macromonomer M-1 (synthesized as disclosed above under Macromonomer Preparation by reaction of two moles of methacrylic acid, two moles of 2,2-bis-[4-(2,3-epoxypropoxy)phenyl]-propane and one mole of adipic acid) comprising 30 percent by weight triethylene glycol dimethacrylate, 10.6328 g triethylene glycol dimethacrylate, 0.0167 g N,N-bis (β-hydroxyethyl)-p-toluidin, 0.5049 g tert. butyl peroxy benzoate, 0.0113 g 2,6-di-tert-butyl-p-cresol.

Immediately before use powder and liquid were mixed in the weight ratio of 1.60 to 1.00 homogenneously. The working time is 4:45 minutes and the setting time is 3.30 minutes. The adhesion to dentine was measured to be 5.2±0.7 MPa. The composite shows the following mechanical properties: compressive strength of 215.3±2.8 MPa, elastic modulus of 3156±53 MPa and a flexural strength of 72.4±7.0.

EXAMPLE 11

Dental Sealer

A dental cement composition is formed from a powder and liquid. The powder is made by homogeneously mixing 25.1820 g silylated strontium-alumo-silicate glass, 1.0773 g silylated strontium-alumo-silicate glass comprising 2 percent by wegith copper thio urea complex and 0.5387 g silylated strontium-alumo-silicaet glass containing 10 percent by weight ascorbic. The liquid is made by homogeneoulsly mixing 18.0000 g of AP-1 comprising 30 percent by weight triethylene glycol dimehtacrylate, 4.5000 g macromonomer M-1 comprising 30 percent by weight triethylene glycol dimethacrylate, 10.6328 g triethylene glycol dimethacrylate, 0.0167 g N,N-bis(β-hydroxyethyl)-p-toluidine, 0.5049 g tert.butyl peroxy benzoate, 0.0113 g 2,6-di-tert.-butyl-p-cresol. Immediately before use the powder and liquid are homogeneously mixed in the weight ratio of 0.80 to 1.00 to form a polymerizing dental sealer composition. This sealer composition is applied to a human dental tooth. The working time is 4.50 minutes and the setting time is 3.45 minutes.

EXAMPLE 12

A dental cement composition is formed from a powder and liquid. The powder is made by homogeneously mixing 99.22 g silylated strontium-alumo-silicate glass, 0.08 g of copper thio urea complex, 0.2 g of ascorbic acid and 0.5 g of Aerosil A 200. The liquid is made by homogeneously mixing 37.373 g AP-1 salt prepared as described in Example 1 and comprising 30 percent by weight triethylene glycol dimethacrylate, 9.343 g of macromonomer M-1, 51.634 g triethylene glycol dimethacrylate, 0.10 g of butylate hydroxy toluene (BHT), 1.5 g tert. butyl peroxy benzoate, (TBPB) and 0.05 g propamine.

Immediately before use the powder and liquid are homogeneously mixed in the weight ratio of 1.60 to 1.00 to form a dental cement, which is then applied to a dental tooth cavity. The working time is 4:45 minutes and the setting time is 3.30 minutes. The adhesion to dentine is measured to be 5.2±0.7 MPa. The composite shows the following mechanical properties: compressive strength of 215.3±2.8 MPa, elastic modulus of 3156±53 MPa and a flexural strength of 72.4±7.0.

EXAMPLE 13

A dental cement composition is formed from a powder and liquid. The powder is made by homogeneously mixing 0.2 g of ascorbic acid, 0.06 g of copper-(I)-thiourea complex, 0.5 g of highly dispersed silicium dioxide, 96.3 g of strontium alumino sodium fluoro phosphoro silicate, and 2.94 g of strontium alumino sodium fluoro phosphoro silicate. The liquid is made by homogeneously mixing 37.373 g of ammonium salt of 2,2,6,6-tetra acryloyl-oxymethyl-4, 8-dioxa 9-oxo-11-undecyl phosphoric acid and N,N-dimethyl aminoethyl methacrylate, 9.343 g of macromonomer obtained by reaction of 2,2-bis-[4-(2,3-epoxypropoxy)-phenyl]-propane, adipic acid and methacrylic acid (I) and further reaction (I) with succinic anhydride, 51.634 g of 1-methyl-1,2-ethanediyl-bis (oxy-2,1-ethanediyl) ester, 1.5 g of tert.-butyl peroxy benzoate, 0.05 g of N,N-bis (hydroxyethyl)-p-toluidine, and 0.1 g of tert.-butyl-p-cresol. Immediately before use the powder and liquid are homogeneously mixed in the weight ratio of 1.60 to 1.00 to form a dental cement, which is then applied to a dental tooth cavity.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A polymerizable composition formed by mixing a first and a second composition;

said first composition, comprising:
   a peroxide, which decomposes by at most fifty percent by weight of said peroxide within 10 hours at 75° C., and
   a polymerizable monomer, said second composition comprising a proton donor, and a metal containing compound, said polymerizable composition having from 0.2 to 5 percent by weight of said peroxide, from 5 to 99 percent by weight of said polymerizable monomer, and from 0.1 to 3 percent by weight of said proton donor, and from 0.02 to 3 percent by weight of said metal containing compound, said polymerizable composition having an initial setting time and a storage setting time measured after storage of said first composition and said second composition for 12 months effectively at a temperature of 23° C., the time period of said initial setting time being within 2 minutes of the time period of said storage setting time whereby the difference between said initial setting time and said storage setting time is less than 2 minutes.

2. The polymerizable composition of claim 1 wherein said second composition has been stored for at least 12 months at a temperature of at least 23° C. prior to said mixing.

3. The polymerizable composition of claim 1 wherein said first composition further comprises from 0.001 to 1 percent by weight of an amine.

4. The polymerizable composition of claim 1 further comprising from 0.001 to 0.5 percent by weight of an amine.

5. The polymerizable composition of claim 1 wherein said first composition further comprises from 0.01 to 0.2 percent by weight of an amine.

6. The polymerizable composition of claim 1 wherein said storage is at a temperature of at least 30° C.

7. The polymerizable composition of claim 1 wherein said storage is at a temperature of at least 43° C.

8. The composition of claim 1 wherein said peroxide is a diacyl peroxide, a perester, a perketale, a peroxy dicarbonate, a dialkyl peroxide, a ketone peroxide or a alkyl hydroxyperoxide.

9. The composition of claim 1 wherein said peroxide is selected from the group consisting of tert-butyl peroxy benzoate, tert.-butyl peroxy (3,5,5-trimethylhexanoate), 2,5-dimethyl-2,5-di(benzolyperoxy)hexane, tert.-butylamyl peroxide, di-(tert.-butyl) peroxide, cumenhydo peroxide, tert.-butylhydro peroxide, tert.-butylperoxy-(3,5,5-trimethylhexanoate) and tert.-butylperoxy-2-ethylhexyl carbonate.

10. The composition of claim 1 wherein said proton donor is an acid, a phenol, a hydroxyl alkene or an acetic amine.

11. The composition of claim 10 wherein said proton donor is an acid selected from the group consisting of sulfinic acid, oxalic acid, picric acid ascorbic acid, barbituric acid and thiobarbituric acid.

12. The composition of claim 3 wherein said amine is an alkyl aryl amine, a dialkyl aryl amine, or a trialkyl amine.

13. The composition of claim 4 wherein said amine is an alkyl aryl amine, a dialkyl aryl amine, or a trialkyl amine.

14. The composition of claim 5 wherein said amine is an alkyl aryl amine, a dialkyl aryl amine, or a trialkyl amine.

15. The composition of claim 1 wherein said metal containing compound is a salt of a metal or an organometallic compound.

16. The composition of claim 15 wherein metal containing compound is an acetate, salicylate, naphenoate, thiourea complex, acetylacetonate or ethylene tetramine acidic acid.

17. The composition of claim 15 wherein said metal of said metal containing compound is selected from the group consisting of copper, silver, cerium, iron, chromium, cobolt, nickel, vanadium and manganese.

18. The composition of claim 1 further comprising a filler and a stabilizer.

19. The composition of claim 1 wherein said polymerizable monomer has at least one polymerizable double bond.

20. The composition of claim 1 wherein said monomer is hydroxypropylmethacrylate, diethyleneglycol dimethacrylate, triethyleneglycol dimethacrylate, 3,(4),8,(9)-dimethacryloyloxymethyltricyclodecane, dioxolan bismethacrylate, glycerol trimethacrylate, furfuryl methacrylate.

21. The composition of claim 1 wherein said monomer is free radical polymerizable.

22. The composition of claim 18 wherein said filler comprises from 10 to 90 percent by weight of said polymerizable composition and is an inorganic filler and/or an organic filler.

23. The composition of claim 1 wherein said composition comprises from 10 to 50 percent by weight of said monomer, 50 to 65 percent by weight of a filler and from 0.2 to 5 percent by weight of said peroxide.

24. The polymerizable composition of claim 18 further comprising from 0.001 to 0.5 percent by weight of said stabilizer.

25. The composition of claim 1 characterized in that the first composition is a powder comprising said proton-donor, said metal containing compound, an amine and fillers and the second composition is a liquid comprising said peroxide, said polymerizable monomer and stabilizers.

26. The composition of claim 1 characterized in that the first composition is a powder comprising said proton-donor, said metal containing compound and fillers, and the second composition is a liquid comprising said peroxide, an amine, said polymerizable monomer and a stabilizer.

27. The composition of claim 1 wherein said polymerizable monomer is a polyalkylenoxide di(meth)acrylate, polyalkylenoxide poly(meth)acrylate, urethane di(meth)acrylate, urethane poly (meth)acrylate, vinyl acrylate, vinylene acrylate or vinylidene acrylate, methacrylate substituted spiroorthoester, methacrylate substituted spiroorthocarbonate, a methacrylate substituted bicycloorthoester or a dimethacrylate of an epoxide.

28. The polymerizable composition of claim 1 wherein said storage is for at least 15 months.

29. A polymerizable composition formed by mixing a first and a second composition;

said first composition, comprising:
a peroxide, which decomposes by at most fifty percent by weight of said peroxide within 10 hours at a temperature of at least 75° C.,
a polymerizable monomer, and from 0.01 to 0.2 percent by weight of amine, said second composition comprising a proton donor, and a metal containing compound, said polymerizable composition having from 0.2 to 5 percent by weight of said peroxide, from 5 to 99 percent by weight of said polymerizable monomer, and from 0.1 to 3 percent by weight of said proton donor, and from 0.02 to 3 percent by weight of said metal containing compound, said polymerizable composition having an initial setting time, said initial setting time being the setting time measured before sufficient storage of said first composition and said second composition, said setting time being started by mixing said first composition and said second composition, and said polymerizable composition having a storage setting time measured after storage of said first composition and said second composition for at least 12 months effectively at a temperature of at least 23° C., the time period of said initial setting time being within 2 minutes of the time period of said storage setting time whereby the difference between the initial and storage setting times is less than 2 minutes.

30. A polymerizable composition formed by mixing a first and a second composition;

said first composition, comprising:
a peroxide is selected from the group consisting of tert-butyl peroxy benzoate, tert.-butyl peroxy (3,5,5- trimethylhexanoate), 2,5-dimethyl-2,5-di (benzolyperoxy)hexane, tert.-butylamyl peroxide, di-(tert.-butyl) peroxide, cumenhydo peroxide, tert.-butylhydro peroxide, tert.-butylperoxy-(3,5,5-trimethylhexanoate) and tert.-butylperoxy-2-ethylhexyl carbonate, and a polymerizable monomer, said second composition comprising a proton donor, and a metal containing compound, said polymerizable composition having from 0.2 to 5 percent by weight of said peroxide, from 5 to 99 percent by weight of said polymerizable monomer, and from 0.1 to 3 percent by weight of said proton donor, and from 0.02 to 3 percent by weight of said metal containing compound, said polymerizable composition having an initial setting time and a storage setting time measured after storage of said first composition and said second composition for 12 months effectively at a temperature of at least 23° C., the time period of said initial setting time being within 2 minutes of the time period of said storage setting time whereby the difference between the initial and storage setting times is less than 2 minutes.

31. A polymerizable composition formed by mixing a first and a second composition;

said first composition, comprising:
a peroxide, an amine, and
a polymerizable monomer, said second composition comprising a proton donor, and a metal containing compound, said polymerizable composition having from 0.2 to 5 percent by weight of said peroxide, from 5 to 99 percent by weight of said polymerizable monomer, and from 0.1 to 3 percent by weight of said proton donor, and from 0.02 to 3 percent by weight of said metal containing compound, said polymerizable composition having an initial setting time and a storage setting time measured after storage of said first composition and said second composition for 12 months effectively at a temperature of 23° C., the time period of said initial setting time being within 2 minutes of the time period of said storage setting time whereby the difference between the initial and storage setting times is less than 2 minutes.

* * * * *